(12) United States Patent
Gondrom-Linke et al.

(10) Patent No.: US 12,399,137 B2
(45) Date of Patent: Aug. 26, 2025

(54) COMPUTER-IMPLEMENTED METHOD FOR MONITORING THE STATUS OF A DEVICE FOR INVESTIGATING OBJECTS

(71) Applicant: Volume Graphics GmbH, Heidelberg (DE)

(72) Inventors: Sven Gondrom-Linke, Heidelberg (DE); Matthias Flessner, Heidelberg (DE); Thomas Günther, Heidelberg (DE); Christoph Poliwoda, Heidelberg (DE); Sören Schüller, Heidelberg (DE); Christof Reinhart, Heidelberg (DE); Daniela Handl, Heidelberg (DE)

(73) Assignee: VOLUME GRAPHICS GMBH, Heidelberg (DE)

( * ) Notice: Subject to any disclaimer, the term of this patent is extended or adjusted under 35 U.S.C. 154(b) by 431 days.

(21) Appl. No.: 17/924,335

(22) PCT Filed: May 10, 2021

(86) PCT No.: PCT/EP2021/062285
§ 371 (c)(1),
(2) Date: Dec. 30, 2022

(87) PCT Pub. No.: WO2021/228747
PCT Pub. Date: Nov. 18, 2021

(65) Prior Publication Data
US 2023/0175988 A1  Jun. 8, 2023

(30) Foreign Application Priority Data
May 11, 2020  (DE) .................... 10 2020 112 651.4

(51) Int. Cl.
*G01N 23/046* (2018.01)
*G01N 23/06* (2018.01)

(52) U.S. Cl.
CPC ............ *G01N 23/046* (2013.01); *G01N 23/06* (2013.01); *G01N 2223/04* (2013.01); *G01N 2223/303* (2013.01); *G01N 2223/419* (2013.01)

(58) Field of Classification Search
CPC .. G01N 23/046; G01N 23/06; G01N 2223/04; G01N 2223/303;
(Continued)

(56) References Cited

U.S. PATENT DOCUMENTS

| 9,743,911 B2 * | 8/2017 | Hedlund ................. A61B 6/487 |
| 2019/0200948 A1 | 7/2019 | He |
| 2019/0265175 A1 * | 8/2019 | Schönfeld ............ G01N 23/046 |

FOREIGN PATENT DOCUMENTS

| DE | 102006048608 A1 | 4/2008 |
| DE | 102017208811 A1 | 11/2018 |

(Continued)

OTHER PUBLICATIONS

German Patent Office, Examination Report for German Patent Application No. 10 2020 112 651.4, mail date Jan. 18, 2021.
(Continued)

*Primary Examiner* — Courtney D Thomas
(74) *Attorney, Agent, or Firm* — SoCal IP Law Group LLP; Angelo Gaz

(57) ABSTRACT

Described is a computer-implemented method for monitoring the status of a device for investigating objects, wherein the investigation of an object involves determining measurement data by measuring the object and operating data of the device is determined during the investigation of the object. The method includes: determining measurement data of the object by means of the device; determining operating data of the device during the determining measurement data of the object; determining at least one quality parameter
(Continued)

from the measurement data; analysing the operating data and the at least one quality parameter; and determining a status characteristic value based on the analysing in order to monitor the status of the device, wherein the status characteristic value indicates a status of the device. The computer-implemented method comparatively easily monitors the functionality of devices for investigating objects during adaptive measurements.

14 Claims, 1 Drawing Sheet

(58) Field of Classification Search
CPC ....... G01N 2223/419; G01N 2223/646; G01N 2223/6466; A61B 6/586; A61B 6/032; G01B 15/045; G01B 21/04
See application file for complete search history.

(56) References Cited

FOREIGN PATENT DOCUMENTS

| | | |
|---|---|---|
| WO | 2015083031 A1 | 6/2015 |
| WO | 2018072832 A1 | 4/2018 |
| WO | 2019230040 A1 | 12/2019 |
| WO | 2021228747 A1 | 11/2021 |

OTHER PUBLICATIONS

European Patent Office, International Search Report and Written Opinion for PCT Application No. PCT/EP2021/062285, mail date Aug. 2, 2021.

* cited by examiner

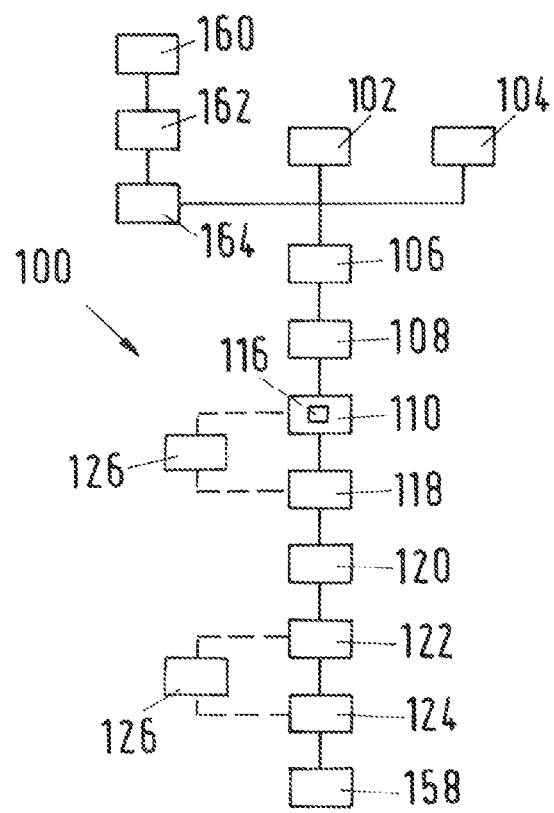
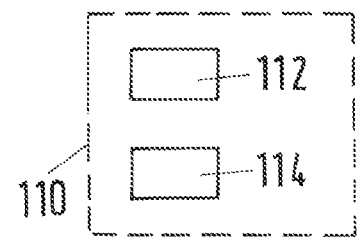
Fig.1
Fig.2
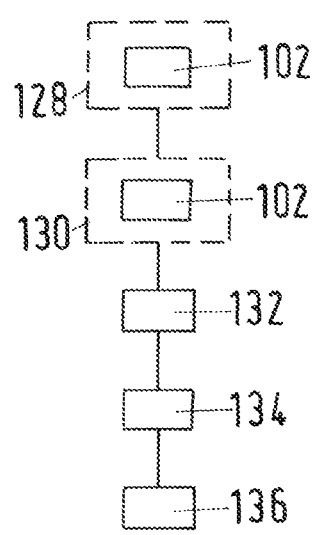
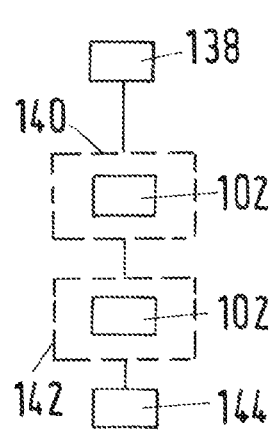
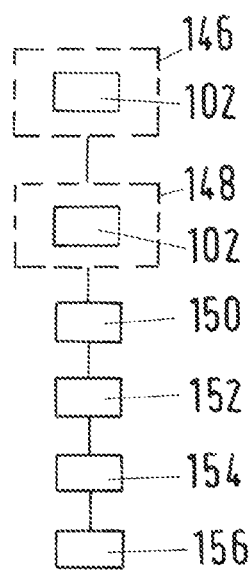
Fig.3a   Fig.3b   Fig.4

COMPUTER-IMPLEMENTED METHOD FOR MONITORING THE STATUS OF A DEVICE FOR INVESTIGATING OBJECTS

RELATED APPLICATION INFORMATION

This patent claims priority from International PCT Patent Application No.PCT/EP2021/062285, filed May 10, 2021, entitled, "COMPUTER-IMPLEMENTED METHOD FOR MONITORING THE STATUS OF A DEVICE FOR INVESTIGATING OBJECTS", which claims priority to German Patent Application No. 10 2020 112 651.4, filed May 11, 2020, all of which are incorporated herein by reference in their entirety.

The invention relates to a computer-implemented method for monitoring the status of a device for investigating objects.

Manufactured objects can be measured by means of devices for investigating objects, e.g. by means of computer tomography or optical sensors, such as photogrammetry or strip projection systems, in order to detect or assess the functionality of these objects. Adaptive measurements can be carried out, which make it possible to make a decision as to the functionality of the object before the complete measurement of the object. As soon as a sufficiently reliable decision can be made, the adaptive measurement can be terminated in order to save time and thus costs. A conventional measurement, on the other hand, performs a complete measurement of the object. The quality of the decision about the measured objects depends on the functional status of the device for investigating objects.

Methods are known in which a functional monitoring of a computed tomography system can be carried out if recurring measurement tasks are to be carried out. With these previously known methods, the functional status of computed tomography systems can only be monitored with great effort.

The object of the invention is therefore to provide a computer-implemented method with which the functionality of devices for investigating objects during adaptive and conventional measurements can be monitored with comparatively little effort.

The main features of the invention are specified herein.

In a first aspect, the invention relates to a computer-implemented method for monitoring the status of a device for investigating objects, wherein the investigation of an object involves determining measurement data by measuring the object, and operating data of the device is determined during the investigation of the object, wherein the method comprises the following steps: determining measurement data of the object by means of the device; determining operating data of the device during the step of determining measurement data of the object; determining at least one quality parameter from the measurement data; analyzing the operating data and the at least one quality parameter; and determining a status characteristic value based on the analysis of the operating data and the at least one quality parameter in order to monitor the status of the device, wherein the status characteristic value indicates a status of the device.

The invention thus provides a computer-implemented method in which the status of the device is monitored by means of a status characteristic value during or after carrying out a measurement of the object, from an analysis of operating data of the device and a quality parameter of the measurement data. This means that while the measurement of the object is still running, operating data of the device are already determined and analyzed together with the previously collected measurement data. The result of this analysis is a status characteristic value that draws a conclusion as to the status of the device. The measurement of the object can be an adaptive measurement, which can be stopped at an early stage as soon as sufficient data about the status of the object is available, and/or based on the available measurement data, optimized imaging parameters for continuing to carry out the measurement are determined. Furthermore, the computer-implemented method according to the invention provides automatic monitoring of the device for investigating objects. Using the computer-implemented method according to the invention, a fault state is automatically determined if the device for investigating objects no longer functions correctly to measure objects with sufficiently high accuracy during an adaptive or conventional measurement procedure. This reduces a user's involvement in monitoring the device for investigating objects.

For monitoring purposes, all information that is present and available during the operation of the device for investigating objects, for example a computed tomography system, can be evaluated, even if it does not appear useful at first glance. By simultaneously acquiring the operating data of the device for investigating objects and the measurement data about the object by means of the device for investigating objects, information from the monitoring can be used in the adaptive or conventional measurement. Furthermore, the simultaneous acquisition of operating data and the measurement data of the adaptive or conventional measurement is optimally monitored and fault states and their causes can be identified if required. The determination of the status characteristic value is the method used to monitor the functional status of the device during the adaptive or conventional measuring procedure.

The status characteristic value can indicate, for example, that the status of the device is acceptable or faulty, i.e. whether a normal status of the device or a fault state is present. Intermediate states are also possible, e.g. if individual detector pixels are defective, so-called bad pixels, but this does not have a significant effect on the measurement results. In this case, the status characteristic value would indicate that there is a certain, but not yet problematic, deviation from a normal status which does not yet cause the device to enter the fault state. In this case, countermeasures can be initiated at an early stage to prevent the occurrence of a fault state.

The measurement data can be final measurement results, in the case of a dimensional measurement, e.g. the diameter of a drilled hole. Furthermore, measurement data can also be raw data that are processed in the measurement chain, in the case of a radiographic measurement e.g. radiographic images or projection data, reconstructed volume data and/or surface data, in the case of a measurement by photogrammetry or strip projection e.g. images of the measurement camera or calculated surface data.

In another example, the step of determining a status characteristic value can comprise the following sub-step: comparing the operating data and the at least one quality parameter with predefined comparative values for the operating data and the at least one quality parameter for determining a status characteristic value.

Predefined comparison values for the operating data and the at least one quality parameter are used in this process, so that the computer-implemented method can decide whether a status of the device is already a fault state or is still a normal status. The comparison is not limited to pre-defining fixed comparison values for individual quantities. It can also be implemented in such a way that several quantities are considered together. For example, if a first quantity A or second quantity B individually deviate by 5% to 10% from a respective normal value, this is not necessarily a fault state. However, in this example, if both quantities deviate from the nominal value by 5% to 10% at the same time, this may be identified as a fault state. The first quantity A and the second quantity B can be operational data and/or quality parameters.

Alternatively or in addition to the use of predefined comparison values, a comparison can be carried out on the basis of predetermined sample data for the operating data and the at least one quality parameter, the sample data being derived from training data. For example, the step of determining a status characteristic value can further comprise the following sub-step: comparing the operating data and the at least one quality parameter with predetermined sample data for the operating data, derived from training data, and for the at least one quality parameter for determining a status characteristic value.

The predetermined sample data thus serve as a kind of reference for the operating data determined during the measurement and the at least one quality parameter. This training data, or sample data, can preferably be used to train a machine learning procedure, e.g. a neural network. The sub-step is then performed by this machine learning procedure. For example, measurements of a reference object can be used to generate training data.

Training data can therefore be collected from different sources. Thus, e.g. fault states can be identified locally on the monitored CT system, e.g. due to abnormally high measurement deviations during the measurement of a master part. This fault state and the characteristics of the monitored quantities can be included in the training data at this time. Furthermore, training data can be collected from computed tomography systems of the same or at least similar design in the same way. In this way, the data base is expanded, while the validity of the result could be somewhat limited due to the possible differences in the characteristics of the computed tomography systems. Furthermore, with the same advantages, data from computed tomography systems with significantly different configurations can also be included in the training data.

In order to create a certain level of comparability for the monitored data from different sources, these can be normalized to typical ranges of values.

For a certain period of time before or after the identified fault state, the temporal profile and the values of the monitored quantities can also be included in the training data.

Furthermore, in addition to fault states, functional states can also be included in the training data in order to identify these also or to distinguish them from the fault states.

Different methods for pattern recognition or from machine learning can be used to determine whether a fault state is present or imminent and, if appropriate, the cause, from the monitored quantities and the available training data. These may include: methods of artificial intelligence, e.g. artificial neural networks, deep learning, support vector machines, Bayes classifiers, nearest-neighbor classification, etc. The at least one method to be used is chosen in such a way that, using the training data, patterns of fault states can be identified in the comparatively large set of the partially nontransparent, supervised data.

The training data can also be generated, for example, from measurement data which is determined by means of the device by means of at least one measurement within a predefined time interval before and/or after determining measurement data of a reference object, wherein the reference object has a known geometry and/or a known property.

The measurements from which the training data is derived need not be measurements of a reference object, nor do they need to have the same or similar geometry as the object to be investigated or being investigated. According to an example, the reference object may have the same or similar geometry as the object to be investigated or being investigated. Only the geometry or the results of the measurements of this reference object must be known. From the comparison of the measurement data and the results of the measurement of the reference object, it is possible to derive the status of the device. Major deviations in this case are an indication of a fault state. In addition to the geometry, other properties of the measured object can also be relevant, e.g. defects in the interior of the reference object, properties of fiber composite materials used, if any, such as fiber diameter, fiber density, and fiber orientation, or material properties such as local density, if applicable.

A reference object can also be referred to as a master part. Master part measurements are performed regularly on a wide range of CT systems to test the functional status of the CT system. Typical repetition rates of such measurements range from several times a day to once a month.

A master part is an object with known geometric properties. These can be external and internal geometric dimensions, as well as material properties such as density, fiber density and fiber thickness or orientation, porosities, or other properties. In order to check the functional status of the computed tomography system, a measurement of this part is carried out and the possibly task-specific measurement results are combined with the reference values or calibration values, which ideally originate from a measurement with a low measurement uncertainty, e.g. compared to a more accurate sensor. The extent of the deviations that occur allows conclusions to be drawn as to whether the computed tomography system is in a functional status for the defined task. If the computed tomography system can successfully perform this measurement task, it can be assumed that its status is "good" and can also perform other similar and sometimes less similar measurement tasks. In order to be able to draw a conclusion about the status when comparing the measurement results with the reference measurement values, limit value intervals for the measurement deviation are usually defined.

These measurements can be used for the training data according to this example. The information to be included in or correlated with the training data as to whether a fault state existed can be derived from the measurement deviations of the master part measurement. For example, the assessment of a "good" or "bad" status can be made based on whether defined limit value intervals of the measurement deviation are not observed. In addition, instead of such a "binary" classification, it is also possible to assess the status of the measuring system with a more detailed resolution, for example "on average 47% of the measurement values within the permitted limit value intervals" or "30% of the measurement quantities tested are outside the limit value intervals".

The respective information as to whether a fault state exists is assigned to the corresponding measurement data of the monitored quantities. For this purpose, the measurement data can be used during the measurement of the master part, as the analyzed measurement deviations have been generated from this.

If it can be assumed that the status of a computed tomography system does not change significantly in a short period of time, measurement data from measurements in a certain temporal environment relative to the master part measurement can also be included in the training data with the assignment to the status derived from the master part measurement. This has the advantage that data from types of measurements that are not represented by the master part are also included in the training data, e.g. if the master part is made of aluminum, while the "temporally surrounding" measurements are based on plastic. This generates training data of plastic measurements. The extent to which this "temporal environment" can reasonably be chosen depends on the stability of the computed tomography system.

In particular, if data are included in the training data that were acquired before the master part measurement, in which a fault state is later determined, a prediction of fault states to be expected in the future can be made, for example, based on patterns in these data.

Alternatively or in addition, the cause of the deviations can also be assigned to the individual master part measurements, in particular those in which fault states have been detected, so that the system can also be trained to predict this. This can also be carried out manually.

The step of determining a status characteristic value may comprise the following additional sub-step, for example: determining whether the status characteristic value indicates a fault state of the device.

In this sub-step the status characteristic value is read out in order to detect whether it indicates a fault state of the device. This is used to identify the fault state, if appropriate. The identification of the fault state can indicate, for example, which of the operating data or the at least one quality parameter form the basis for the fault state. In this way, the fault in the device for investigating objects can be automatically localized using the computer-implemented method.

In this case, a fault state means a status in which the accuracy of the measurement decreases so much that the measurement tasks to be performed can no longer be carried out in a meaningful manner. This can therefore be defined for specific measuring tasks, e.g. on the basis of the tolerances that are to be checked according to the measurement plan, but also specifically for a computed tomography system, e.g. based on a global specification or minimum accuracy. Depending on the definition, a moderate deterioration of the status of the computed tomography system which only causes a slight deterioration of the measurement accuracy can therefore still be evaluated as not a fault state in a computed tomography system with comparatively poor specification or in measuring tasks with comparatively large tolerances. Nevertheless, this deterioration can be identified and an initial warning can be issued or countermeasures can be initiated.

According to another example, the method can further comprise the following step if the status characteristic value indicates that a fault state of the device might be present: determining measurement data of a reference object by means of the device; and analyzing the measurement data of the reference object to determine information relating to whether the device is in a fault state.

In this example, a reference object is measured by means of the device for investigating objects, in order to determine measurement data of the reference object if there is a suspicion that a fault state of the device is present. One possibility is that the current measurement is interrupted to measure a reference object. Alternatively, it is possible to wait until any active measurement is completed until a reference object is measured. The measurement data of the reference object is used in carrying out an analysis to determine whether the device is in a fault state.

In other words, if it turns out that a fault state could be present but it is not possible to determine on the basis of the current database whether a fault state is actually present or what the cause of the fault state is, a kind of self-diagnosis can be requested or carried out.

For this purpose, a suitable reference object, a so-called master part or etalon, ideally with known geometry, is measured with suitable imaging parameters to generate measurement data that can be analyzed in a targeted way to obtain more information about the causes of the fault state. The selection of which master part or etalon should be measured and with which imaging parameters in order to generate as much new information as possible or the missing information in a targeted manner, can be made within the context of the method. Thus, if multiple other causes of faults are possible on the basis of the available data, a measurement can be selected which can differentiate between exactly these causes.

In an example, if increased blurring is detected in the volume data and it cannot be clearly assessed whether this is due to an enlarged focal spot or in incorrect geometric calibration, a single irradiation of a small object can be carried out, e.g. a small sphere or a wire, with a high geometric magnification. No reconstruction is necessary for this. If the blurring of this projection is not increased, the focal spot can be ruled out as the cause. In this case, the incorrect geometric calibration is the most likely cause, as this does not affect the blurring of projections.

In another example, if it is not clear whether an incorrect geometric calibration or drift effects are the cause of a fault state, a fast scan, e.g. with a small number of projections, and a slow scan, e.g. with a large number of projections, of an object can be performed with otherwise identical imaging parameters. If the fault state only occurs during the slow scan, the cause is probably a drift effect. If the problem still occurs during fast scanning, the cause is probably not a drift effect, but an incorrect geometric calibration. By means of further tests, e.g. at different magnification levels, the method can further narrow this down.

Ideally, these measurements can be performed automatically with the aid of a part exchange. Alternatively, or in addition, a user can be instructed to carry out this measurement. Furthermore, in the ideal case, various master parts or etalons are available for this measurement.

These self-analysis steps can be performed as soon as an imminent fault state is suspected.

In another example, the method can additionally comprise the following step: determining a fault cause parameter at least from the status characteristic value, wherein the fault cause parameter indicates a possible cause of the fault for a fault state.

The fault cause parameter can be used to determine a possible cause of a fault state. The following step can also be preferably carried out to determine the fault cause parameter: comparing the operating data and the at least one quality parameter with predefined comparative values for the operating data and the at least one quality parameter for determining which potential fault cause exists. The operating data and quality parameters that are responsible for the fault state are thus determined from the comparison of the operating data and the at least one quality parameter with predefined corresponding comparison values. In this way, a possible fault cause for the fault state can be determined. This narrows down the search for causes of the fault state for a user and saves time and costs.

Therefore, in the event of a fault state, not only is the information represented by the state characteristic value output, "that something is wrong", which is a helpful piece of information in itself since a user then at least knows that a troubleshooting procedure must be started, but an indication is also given as to where the troubleshooting should start. Ideally, it can be predicted even before a fault state occurs that a fault state will occur in the near future, e.g. that in the case of a computed tomographic device the X-ray source is displaying initial power fluctuations, which was detected by a greater variation in the gray value level in the background of the projection data. It can therefore be assumed, according to that example, that major problems of the X-ray source are to be expected in the near future.

According to an example, the monitored quantities can be used to determine whether a fault state is present and, if so, what the cause of this could be, for example, by using a table or decision tree.

An example of this may be to set specific limits for the quantities to be monitored. It is then checked whether these limits are exceeded or undershot. This gives an initial indication of a possible fault state. Based on the information as to which quantities do not comply with the limits and in which direction and to what extent the limits are exceeded, possible causes of faults can be derived from prior knowledge.

For example, it may be determined that the volume data is unusually blurred, i.e. the point spreading function is unusually broad. At the same time, however, no abnormally high blurring was found in the projection data. Thus, it is unlikely that an enlarged spot, e.g. due to defocusing of the electron beam, is the cause, as this would also be reflected in the projection data. A possible cause would be a misalignment of the system, i.e. the location and orientation of the source, detector and turntable in space are not known precisely when the volume data is reconstructed. This results in blurred volume data. This result of the analysis can be passed on to the user. This is an example of the use of a decision tree to determine the cause of a fault.

Possible fault causes could be specified for each of the monitored quantities, which could lead to a violation of the limits. Even if limits are violated by two or more quantities at the same time, appropriate possible fault causes could be specified. Conversely, it is of course also possible to specify for the fault causes the quantities for which they would typically cause a violation of the limits. These are examples of using appropriate tables to determine the cause of a fault.

These specifications could be manually defined. However, for past fault states, possibly with a known cause, the corresponding quantities that were outside of limit intervals can also be stored, and in this way a database can be built up over time, possibly automatically.

In another example, no fixed limits need to be defined, but empirical values that can be automatically adjusted can be used to identify abnormalities in this way. Abnormalities can include such things as the temperature in the measurement volume being 3° C. above the mean value of the last week, or if the background noise in the projections is two standard deviations above the mean value of the last month.

In summary, this approach is best used to identify the sort of relationships between monitored quantity and fault state (possibly including cause), which are comparatively obvious and describable for an expert.

For example, if the fault cause parameter could not be determined, the method may further comprise the following step: determining measurement data of a reference object by means of the device; and analyzing the measurement data of the reference object to determine information for determining the fault cause parameter.

This step can be performed alternatively or in addition. If no fault cause parameter was able to be determined, a reference object is thus measured by means of the device in order to determine reference measurement data. This reference measurement data is analyzed to determine the cause of the fault. The cause of the fault can be determined, for example, from the deviations between the results of the measurement data of the reference object and the measurement data of the object to be measured from known reference values. The operating data can also be analyzed in the same way. The advantage of using a reference object is that typically more, or more accurate, reference values are available for this. Thus, even in the case of a fault cause parameter that cannot be determined in previous steps, the computer-implemented method can also determine a fault cause parameter with this step and facilitate a troubleshooting process for a user.

Furthermore, for example, if in the step of determining a fault cause parameter a fault cause parameter is determined which indicates that a geometric calibration of the device has an accuracy value that is outside a predefined accuracy value interval, the method can further comprise the following step: calibrating the device.

A calibration of the device is carried out according to this example if the fault cause parameter indicates that the geometric calibration of the device is incorrect, i.e. has an accuracy value that is outside a predefined accuracy interval. That is, if the computer-implemented method reveals that the cause of the fault is the incorrect calibration of the device, the computer-implemented method automatically causes a calibration of the device in order to increase the accuracy value for the geometric calibration of the device, so that the accuracy is once again within the predefined accuracy value interval. For example, the accuracy interval can be between 95% and 100%, with 100% representing the maximum accuracy of the geometrical calibration. However, any interval between 0% and 100% can be selected.

If the fault state indicates that the geometric calibration is impaired, an increased measurement uncertainty can be expected. The accuracy interval can be defined with respect to general requirements or with respect to a specific measurement task. For dimensional measurements, the uncertainty of the measurement itself can be estimated, e.g. based on the voxel size error. For the analysis of pores, limits for blurring of the data can be defined.

If as a result it turns out that the functional state of the computed tomography system is not adequate, a so-called calibration procedure for geometric calibration can be requested or carried out. This may mean that a user is prompted to perform such a calibration procedure. If possible, this can be carried out by the method. A calibration procedure usually means that a special etalon, which usually consists of one or more spheres, is positioned in the beam path, possibly at different positions, and irradiated. Based on the radiographic image, e.g. B. using the imaged positions of the spheres, the geometry of the computed tomography system can be acquired. In axial CT, this can generally be modeled by nine degrees of freedom: position and orientation of detector and position of the X-ray source, in each case relative to the rotary table. With free trajectories, this geometric calibration can also be much more complex, with a larger number of degrees of freedom. The acquisition of this geometry is called geometric calibration. On this geometry, the reconstruction can be carried out or parameterized so that a way that volume data can be calculated that are as error-free and sharp as possible.

This calibration process can be carried out completely automatically, e.g. by positioning the etalon used in the measuring volume or on the rotary table by means of a part exchanger controlled by the measuring system.

For example, a calibration can also be carried out preventively if a fault state of the device is indicated. This means that even if the cause of the fault is unknown, i.e. if the fault cause parameter could not be determined, a calibration of the device can be carried out as a precaution. With the precautionary calibration of the device, it is at least possible to rule out the geometric calibration of the device being the cause of the fault if the newly determined status characteristic value after the calibration continues to indicate a fault state.

However, it is also possible to perform a geometric calibration based on the acquired projection data of a normal measurement, completely without a real etalon. In this case, e.g. based on the available measurement data or projections, the geometric calibration that best matches the data can be determined. This can also be carried out retrospectively for measurements that have already been carried out.

Further, the device can, for example, have an automatic object exchange unit, wherein the method further comprises the following step: substituting a reference object for the object into the device for investigating objects for determining measurement data relating to the reference object and/or substituting a calibration object for the object into the device for investigating objects to calibrate the device for investigating objects.

In one example, the object exchange unit has a robot arm that can grip an object, possibly including a support for the object, and place it in the beam path or on the rotary table.

In another example, the object exchange unit has at least one rotary table that can be moved from below towards a battery of objects or supports and, possibly using a suitable support, can pick up the objects. None of the examples requires a user action.

According to an example, the method can further comprise the following steps: carrying out at least the step of determining measurement data of the object with a first object, wherein the measurement is a radiographic measurement; carrying out at least the step of determining measurement data of the object with a second object, wherein the measurement is a radiographic measurement; determining imaging parameter sets of the device which are identical for the determination of measurement data for the first object and for the determination of measurement data for the second object; determining first projection representations from the measurement data for the first object by means of the determined imaging parameter sets, and determining second projection representations from the measurement data for the second object by means of the determined imaging parameter sets; and analyzing at least one first quality parameter assigned to one of the first projection representations, and at least one second quality parameter assigned to at least one of the second projection representations, for differences. In an alternative or additional example, the method may further comprise the following steps, if an imaging parameter set of a first object and an imaging parameter set of a second object are at least partially not identical: defining imaging parameter sets of the device for determining measurement data; carrying out at least the step of determining measurement data of the object with a first object with the defined imaging parameter sets for determining first projection representations, wherein the measurement is a radiographic measurement; carrying out at least the step of determining measurement data of the object with a second object, with the defined imaging parameter sets for determining second projection representations, wherein the measurement is a radiographic measurement; and analyzing at least one first quality parameter assigned to one of the first projection representations, and at least one second quality parameter assigned to at least one of the second projection representations, for differences; wherein a geometry of the second object differs from a geometry of the first object within a predefined tolerance interval.

Radiographic measurements can be, e.g. X-ray measurements, e.g. radiography or computed tomography.

Imaging parameters of a projection can be the radiographic geometry of the projection and/or setting options that can be set when an object is irradiated, such as current and voltage of the X-ray source, the exposure time or the selected filter.

A radiographic geometry describes the direction in which the object is irradiated during the radiographic measurement, the position of the irradiated region and the magnification. In an X-ray measurement or radiographic scan this geometry is therefore described by the position of the X-ray source and the detector relative to the measured object, resulting in nine geometric degrees of freedom. This results in three translational degrees of freedom for the X-ray source and the detector, and three further degrees of rotational freedom for the detector. A radiographic geometry can be defined with respect to the object or with respect to the device for investigating objects.

In the step of analyzing at least one first quality parameter assigned to one of the first projection representations, and at least one second quality parameter assigned to at least one of the second projection representations, for differences, not only quality parameters of the projection representations themselves can be analyzed, but also, for example, quality parameters of volume data reconstructed from the projection representations.

This is used to monitor measurements in which at least partly different imaging parameters, for example partly different radiographic geometries or trajectories for measurement objects of the same or similar geometry are traversed. In a first alternative, for the analysis of the functional status, between at least two measurements in each case, a set of projection representations is identified for which the radiographic geometry and the remaining imaging parameters were identical. These are compared and evaluated to determine a difference in the quality parameters of the two measurements. In the second alternative of the example, projection representations with the same radiographic geometry and the same settings are acquired and analyzed.

This enables a reference or a common database to be established between different measurements, in particular adaptive measurements.

In the second alternative, the comparability between a large number of measurements is established by the targeted creation of identical projections. Additional time must be allowed for this. Conventional methods for monitoring that analyze this data and examine it e.g. for drifts, can be used for this. These can either compare the identical projections directly, or volume data can be determined and analyzed based on a reconstruction from identical projections. To analyze this data for monitoring, the above mentioned methods can be mentioned.

In the first alternative, such a comparison is enabled between at least two measurements, wherein these measurements can be "adjacent" in time. A comparison is thus initially only possible for a comparatively small number of measurements. If such a comparison of a quality parameter is known, for example, between measurements A and B and for B and C, a comparison of A and C can be performed, at least qualitatively, for which a quality parameter should be used which has a certain transitivity in this respect. In this way, many different measurements can be compared or monitored in a "concatenated" fashion, thus enabling a long-term monitoring to be carried out, even if each individual measurement can only be compared directly with comparatively few measurements. This analysis can also be performed on the basis of projections and/or reconstructed volume data.

Both alternatives require that the measurement objects of the individual measurements have at least a similar geometry, e.g. an identical target geometry.

A combination of these two alternatives would be to define certain standard projections during the measurement, from which the required projections can be selected flexibly for each measurement. This restricts the selection of the "allowed" projections. If enough standard projections are defined, without greatly limiting flexibility the probability that two measurements can be compared increases, or the average number of projections that can be compared between two measurements increases. These standard projections can also be calibrated separately or selectively during a calibration process in order to increase accuracy. This is advantageous in particular in robot CT, where the positioning accuracy is comparatively low but the "selection" of the radiographic directions is extremely large.

In another example the method can comprise the following steps: carrying out at least the step of determining measurement data of the object with a first object, wherein the measurement is a radiographic measurement; carrying out at least the step of determining measurement data of the object with a second object, wherein the measurement is a radiographic measurement, wherein a different radiographic geometry is used than for the first object; determining projection representations from the measurement data of the first object; determining projection representations from the measurement data of the second object; comparing at least one blurring between the projection representations of the first object and the projection representations of the second object; and analyzing the at least one blurring to determine the status characteristic value.

In this example, measurements are monitored in which different radiographic geometries or trajectories are used, as can be the case with adaptive measurements, for example. The blurring of the image is determined from the projection data and analyzed to monitor the functional status.

For this purpose, it is advantageous to compare projection representations with the same setting options, although the radiographic geometry may differ. With regard to the radiographic geometry, it may be advantageous to compare projections of identical or similar geometric magnification, wherein the other geometric parameters may differ. This ensures that in X-ray scans, for example, the blurring caused by the spreading of the X-ray spot is expressed similarly in the measurement data, allowing a more robust comparison.

The advantage of analyzing the blurring in the projection image data is that it is comparable over many measurements, regardless of the geometry of the scanned object or from which direction it is irradiated. These remaining influencing variables, which vary between the measurements, e.g. the imaging parameters, in particular the resulting focal spot size and the geometric magnification, can be quantified comparatively easily and their influence on the blurring of the projections can be calculated.

However, it is not trivial to determine the blur or point spreading function produced by the imaging system in the projection data. The problem is that the radiation does not form a sharp edge from light to dark in the projections, since the gray value depends on the irradiation length. When an object is exposed to radiation, the irradiation length usually increases continuously. If e.g. a sphere is irradiated, the gray-value profile exhibits a gradient from the edges of the sphere to its center. This gradient suggests a blurring, but one which is caused by the geometry of the irradiated object and not by the blurring of the computed tomography system itself, which is to be determined. A real gray value curve is obtained to a first approximation from the theoretical gray value curve caused by the object, which is convolved with the point spreading function of the imaging system. However, this point spreading function is extremely small compared to the gray-level gradients caused by the object. This makes it difficult to separate these two effects, in particular if the geometry of the object being irradiated is not known exactly. However, if the theoretical gray-level gradient caused by the object forms a sharp edge, the blurring caused by the point spreading function can be more easily determined. However, this case rarely occurs, because many surfaces are either not sufficiently flat and show certain deviations, which in turn cause a false blurring, and nor is it known precisely in which projections, if any, planes are irradiated in a correspondingly "sweeping" manner. The identification of the regions to be evaluated is therefore not trivial.

If in an example the geometry of the measurement object is known in principle, e.g. by prior knowledge, such as a representation of the object with CAD, an irradiation direction can be specifically set up in which a maximally sharp edge is formed in the radiographic images, which can be analyzed with regard to the blurring. In this case, prior knowledge about the expected blur caused by the geometry can also be used and from this the influence or blurring of the measurement system can be separated from the measured blurring.

If in another example the geometry is not known in advance, an evaluation of the, possibly preliminary, measurement data can be carried out, e.g. a reconstruction and a surface determination, to determine the geometry. Similarly, this can be used to identify suitable areas in the projection data that have suitable edge transitions.

In another example, the spatial frequencies that occur, including the respective amplitude or contrast, in all projections can be analyzed or statistically evaluated. For example, in a histogram the peak at the highest spatial frequency, which is clearly visible, could be a measure of the blurring. This can be, for example, the transitions that coincidentally meet a transition that allows the point spread function to be sufficiently determined. If necessary, high-frequency components caused by noise must be identified and excluded from the analysis.

In another example, in addition to the measurement object, a suitable, ideally known, geometry can also be acquired, e.g. a small sphere or wire. Accordingly, a suitable edge transition is available in the projection data that can be evaluated.

According to another example, the method can additionally comprise the following step: determining an estimate of an uncertainty of a measurement variable of the object determined from the measurement data by means of the operating data and the at least one quality parameter.

For this purpose, information can be gathered from a wide variety of sources to estimate the measurement uncertainty of a measurement, e.g. empirical values, an analysis of the current data quality, or statistical analyses of the stability of a measurement result. Monitoring the functional status of the computed tomography system used can provide additional useful information that can be fed into the uncertainty assessment.

For example, it may be known from the monitoring that the geometric calibration already has a certain level of uncertainty, which in turn has a negative effect on the measurement uncertainty of the measurements to be performed. Accordingly, an increased "base level" of the measurement uncertainty can be taken into account in the measurement uncertainty determination in order to determine more realistic values of the uncertainty. It is also possible to allow for the fact that an uncertainty or slight disturbance of the geometric calibration affects different measurement variables in different ways, for example more strongly on longer measurement variables.

In another example, an increased noise level of the data can be detected in the monitoring, e.g. due to a lower power of the X-ray tube. This increases the uncertainty of the measurement variables. Here, the sensitivity of the individual measurement variables to the fault state can also be taken into account: for example, the measurement of a shape deviation reacts significantly more strongly to an increased noise level than the measurement of a distance between sphere centers.

During the step of determining measurement data of the object by means of the device, the following steps can be performed, for example: determining preliminary measurement data and/or at least one preliminary quality parameter from the measurement data; adapting the step of determining measurement data of the object by means of the device, taking the preliminary measurement data and/or the at least one preliminary quality parameter from the measurement data into account.

In this example, the information accrued during a measurement can be used during the measurement to optimize the measurement or the imaging parameters to be used.

According to another example, the method can also comprise the following step: determining whether a measurement variable of the object determined from the measurement data, preferably taking an uncertainty of the measurement variable into account, lies within a predefined tolerance range.

In this case, a reliable conclusion means that the measurement result is either certainly within or certainly outside the tolerance range, taking the uncertainty into account.

In this way, the regions in which a reliable conclusion is not yet possible can be identified. In this case, additional information primarily for this region can be collected during the measurement. This is not necessary for regions where a reliable conclusion is already possible. This saves time when recording measurement data.

Furthermore, the measurement procedure can be terminated, if necessary prematurely, if a reliable statement is possible for all variables and/or for a critical variable if it is possible to conclude reliably that the variable is outside the tolerance range.

The determination of the uncertainty can use information from the monitoring.

The information from the monitoring, i.e. the current status of the device for investigating objects, e.g. of a CT system, can be fed into a digital twin of the device in order to keep it current or as identical as possible to the real device. This has advantages when using the digital twin, which can be e.g. a simulative measurement uncertainty determination.

A further aspect of the invention relates to a computer program product having instructions executable on a computer, which when executed on a computer cause the computer to carry out the method in the preceding description.

Advantages and effects as well as further developments of the computer program product arise from the advantages and effects as well as further developments of the above described method. In this respect, reference is therefore made to the preceding description. For example, a computer program product can mean a data carrier on which a computer program element is stored, that contains instructions that can be executed for a computer. Alternatively, or in addition, a computer program product can also mean, for example, a permanent or volatile data store, such as flash memory or RAM, that contains the computer program element. However, other types of data stores that contain the computer program element are not excluded.

Further features, details and advantages of the invention emerge from the wording of the following description of exemplary embodiments on the basis of the drawings. In the drawings:

FIG. 1 shows a flowchart of an example of the computer-implemented method with optional steps;

FIG. 2 shows a flowchart of further optional steps of the method;

FIG. 3a, b shows a flowchart of further examples of the method with further optional steps; and FIG. 4 shows a flowchart of a further example with further optional steps.

In the following, the computer-implemented method for monitoring the status of a device for investigating objects is referenced in its entirety with the reference sign 100. The investigation of the object using the device comprises determining measurement data by means of a measurement of the object and determining operating data of the device during the investigation of the object.

FIG. 1 shows an example of the computer-implemented method 100. In a first step 102, measurement data of the object is determined by means of the device for investigating objects. This measurement can be, for example, a radiographic measurement by means of a computed tomography system. For example, the measurement data can be two-dimensional projection image data. Alternatively, or in addition, the measurement data may be volume image data reconstructed from the projection image dataset, or surface data determined from the volume image data. If the device uses a different measurement method or a different sensor, different data is defined as measurement data accordingly.

During step 102, step 104 is performed simultaneously, in which operating data of the device is determined.

Operating data of the device may be, for example, dark current and light current of a detector of the device, i.e. pixel-resolved information that is used for light-dark matching or flat-field correction. This can also be, e.g., the number and distribution of defective pixels of the detector or measuring camera. These are usually identified by certain methods and stored as a mask.

In relation to a rotary table, these can be operating quantities such as voltage and current. They can also be geometric parameters such as tilt and concentricity. External sensors, e.g. laser interferometers, can also be used. "Internal sensors" can also be used by irradiating a suitable or dedicated object from different angles and evaluating the image on the detector. For example, a spiral arrangement of spheres is well suited for this purpose, since the spheres do not shade each other on the detector and their position in the beam path can accordingly be calculated accurately. Such a measurement is often carried out during the regular calibration process. Therefore, corresponding properties or variables/parameters of the last calibration process performed can be monitored.

With regard to an X-ray tube/source of the device, the operating data may be the current curve, the voltage curve, the focusing and centering currents, or the difference between tube and target current.

Operating data can also include e.g. device information: the temperature, for which different measuring points are possible, e.g. outside the device, inside a radiation protection booth, on a detector, a tube, a rotary table, on the axes, or on the measurement object. The time of day, the duration since the last extended period in which the measuring device or its components were deactivated, the duration since the last light-dark adjustment, the time since the last maintenance or since the last calibration process, can also be operating data.

In addition, basic information about the configuration, manufacturer and construction of the computer tomography system used, e.g. cone beam, fan beam, or robot CT, can be used as operating data. It is also possible to take into account the imaging parameters selected during the measurement, e.g. the duration of the scan, exposure time per projection, the image averaging per projection, the nominal voltage, nominal current, pre-filtering, geometric magnification, or the nominal voxel size for use as operating data.

In addition, meta-information about the object to be measured, e.g. the target geometry or material, can be operating data.

In the case of an iterative reconstruction, the convergence speed of the reconstruction can be used as operating data.

At least one quality parameter is determined from the measurement data in step 106. Quality parameters can be e.g. a, possibly local, match between the gray values of the projections and a forward projection of reconstructed volume data. This can be a measure of the consistency of the volume data with the projection data. If the level of matching is low, artifacts or image errors can be expected in the volume data. Furthermore, an analysis of the uniformly illuminated background in projections can be made in terms of homogeneity, the mean gray value, the signal-to-noise ratio, or the noise power spectrum. Further, this can be the blurring or the point spreading function in the projections.

Quality parameters can be derived from, for example, measurement data available as volume data, as an analysis of gray values of the volume data with regard to their quality in the environment of the surface, where the focus can be in particular on the blurring or the point spreading function and the deviation from an ideal model gray-value transition since the quality parameters determined in this way are determined precisely on the basis of the data that affect the result of the surface determination, wherein the surface is in turn important for many evaluations if the significance of these quality variables is particularly great.

An analysis of homogeneous regions of the volume data can also be performed, e.g. the background or the homogeneous material, in terms of signal-to-noise ratio and homogeneity. This analysis is facilitated by the fact that prior knowledge of these image regions exists in the form of a model, ideally of constant gray values in the material and in the background. Deviations from this are probably due to data quality and not to changes to the object.

Furthermore, an analysis of a gray-value histogram of measurement data present as volume data can be carried out, e.g. in terms of the spacing and width of the individual material peaks.

If defects have been detected, the volume data in these regions can be analyzed with the knowledge of the existing defects, e.g. concerning the blurring or point spreading function or the contrast.

Furthermore, an analysis of the surface determined from the volume data can be carried out, e.g. with regard to surface properties such as shape deviations and parameters relating to ripple or roughness.

The above-mentioned quantities, both the operating data and the quality parameters, can in principle be acquired with different temporal resolutions, wherein the possibilities can vary between the quantities to be monitored. Sampling can be performed continuously, quasi-continuously with a high sampling rate, or with a fixed frequency in time. In addition, a measurement variable can be acquired for each acquired projection or for each of a predefined number of acquired projections. In addition, a measurement variable can be acquired for specific events, e.g. start and end of a measurement, the opening of the protective cabin of the CT system, or after performing a light-dark calibration.

In a further step 108, the operating data and the at least one quality parameter are analyzed. The analysis indicates whether a fault state is present in the device for investigating an object.

For this purpose, in step 110 a status characteristic value is determined, which is based on the analysis of the operating data and the at least one quality parameter. The status characteristic value indicates the status of the device. This can be a fault state or a normal state. The status characteristic value can also indicate one or more states between the fault state and the normal state. These states between the fault state and the normal state describe ambiguous states in which it is not clear whether the status is a fault state or a normal state. The closer an intermediate state is to the normal state or the fault state, the higher the probability that a normal state or fault state is present.

Step 110 may optionally have a sub-step 116, in which it is determined whether the state characteristic value indicates a fault state of the device. This means that when determining the status characteristic value, the status characteristic value is initially not further evaluated. An evaluation of the status characteristic value is carried out only by determining in sub-step 116 which status characteristic value is now present.

If an intermediate state has been identified with the status characteristic value, measurement data of a reference object can be optionally determined by means of the device in step 118. For this purpose, in a further optional step 126, a reference object can first be substituted for the object in the device for investigating objects, in order to determine measurement data about the reference object. In this case, the device for carrying out this step 126 has an automatic object exchange unit.

In another optional step 120, the determined measurement data of the reference object and, if necessary, the operating data can be analyzed during the measurement of the reference object. This is used to determine information as to whether a fault state of the device is present. This can be used to improve the information provided by the status characteristic value that only indicates an intermediate state, indicating that there might be a fault state.

A fault cause parameter can be determined from the status characteristic value in another optional step 122. The fault cause parameter indicates a possible fault cause of the fault state. However, in many cases, the fault cause parameter does not provide accurate information about the cause of the fault state.

If in step 122 a fault cause parameter is determined that indicates that a geometric calibration of the device is not acceptable, i.e. if the geometric calibration of the device has an accuracy value which is outside a predefined accuracy value interval, the further step 124 is carried out in which the device is calibrated. For this purpose, step 126 can optionally be carried out, wherein the device then has an automatic object exchange unit. In step 126, which is performed instead of step 124, a calibration object is substituted for the object in the device for investigating objects.

The calibration object has a known geometry, so that the device for investigating objects can be calibrated accordingly.

In a further optional step 158, an estimated value can be determined, which indicates an uncertainty of a measurement variable of the object determined from the measurement data. The estimated value is determined on the basis of the operating data and the at least one quality parameter.

In another optional step 160, preliminary measurement data is obtained during step 102. In addition, alternatively or additionally, at least one preliminary quality characteristic value is determined from the measurement data obtained in step 102.

With the preliminary measurement data or with the preliminary quality characteristic value, step 102 is adjusted in another optional step 162. An adaptive measurement is thus carried out, the measurement parameters of which can be changed during the measurement procedure on the basis of the results obtained so far, which can be based on preliminary measurement data or on preliminary quality parameters.

Further, after steps 160 and 162, the optional step 164 can be carried out, in which it is determined whether a measurement variable of the object determined from the measurement data lies within a predefined tolerance range. For example, a measurement variable of the object can be a length of one side of the object. For example, it can also be a thickness or density at a specific location or in a specific region in the object. If the measurement variable is within a predefined tolerance range, wherein the predefined tolerance range can be specified by a target geometry, the adaptation of the measurement or of step 102 is considered successful.

Furthermore, step 164 can be carried out taking an uncertainty of the measurement variable of the object into account. This means that a success of the adaptation is assumed only if this measurement variable is within the predefined tolerance range, even if the uncertainty of the measurement variable is taken into account.

FIG. 2 shows a flowchart of step 110 with optional sub-steps 112 and 114. The two sub-steps 112 and 114 can be provided independently of each other.

Sub-step 112 relates to a comparison of the operating parameters with predefined reference values for the operating data and to a comparison of the at least one quality parameter with predefined comparison values for the at least one quality parameter. The comparison is used to determine the status characteristic value.

The computer-implemented method 100 can determine by means of the comparison whether deviations exist between the operating parameters and their reference values or deviations between the at least one quality parameter and its comparison value. If there are deviations, this may be a sign that there is a deviation from the normal state of the device. The status characteristic value is therefore set either to indicate an intermediate state or a fault state.

Sub-step 114 relates to a comparison of the operating parameters with predetermined sample data derived from training data for the operating data and to a comparison of the at least one quality parameter with predetermined sample data derived from training data for the at least one quality parameter. This comparison is also used to determine the status characteristic value.

In this case, by means of the comparison from sub-step 114 the computer-implemented method 100 can determine whether deviations exist between the operating parameters and the sample data for the operating parameters or deviations between the at least one quality parameter and its sample data. The sample data are based on training data which were used to determine the sample data before sub-step 114. Deviations between the operating data and its sample data or the at least one quality parameter and its sample data indicate a deviation from the normal state of the device. The status characteristic value is therefore set either to indicate an intermediate state or a fault state.

The sample data can be determined, for example, from a simulation that works with the training data as input data. For this purpose, simulation tools can be used that can realistically simulate the entire measurement or radiographic process including the reconstruction and further data evaluation. In this way, a large amount of training data can be generated with little effort and in a targeted manner, in which defined fault causes and their effects on the measurement data are included. Any and/or different causes of faults can be simulated, both separately and in different combinations.

The advantage is that the specific properties of the device used to investigate the object, e.g. a CT system, can also be simulated. This will make the generated training data better matched to the CT system being monitored. A measurement task-specific training is also possible, by scanning the same objects in the simulated measurements that are also to be measured in the real controlled mode.

Alternatively, a reference object is first investigated and from this, it is determined whether a fault state exists. The geometry of the reference object can differ from the geometry of the actual object to be measured. Training data can be determined directly from this.

Furthermore, further measurements of other objects to be measured can also be made in the temporal environment of the measurement of the reference object to be measured, i.e. shortly before and/or shortly after it. The geometry or geometries of the other objects to be measured can in turn differ from the geometry of the reference object and the object to be measured. In addition, the geometry of the other objects does not have to be known or no reference measurement results need to be available to be able to estimate whether a fault state is present for each of these measurements. This information is taken from the "temporally nearby" measurement of the object to be measured, i.e. it is assumed that the status of the device has not changed significantly in this short period of time.

In this way, additional training data can be generated in the normal measurement mode without additional reference measurements.

Training data can be generated in another example by using information from maintenance procedures. If it is determined from the maintenance procedures that a certain fault was present, the characteristics of the monitored data before this time can be assigned to this fault, even retrospectively. In addition, an analysis of the differences in the characteristics of the data before and after the maintenance, in which the fault was corrected, can be carried out to identify the relevant characteristics. It is thus possible to detect the corresponding fault earlier in the future.

For this purpose, e.g. for example, a manufacturer of CT systems can set up appropriate databases of training data over many maintenance procedures for monitoring purposes for its CT systems, possibly divided by design types, and make them available to users.

Furthermore, fault states of a CT system can also be induced deliberately in order to analyze their effects on the data quality and to include them in the training data.

FIGS. 3*a* and 3*b* relate to further exemplary embodiments of the computer-implemented method 100, in which a first and a second object are measured to determine quality parameters. The geometry of the second object differs only slightly from the geometry of the first object, i.e. the geometry of the second object is within a predefined tolerance interval of the geometry of the first object.

According to FIG. 3*a*, the method 100 may comprise step 128, which comprises at least step 102 and is carried out with the first object. Step 102 is carried out by means of a radiographic measurement of the first object. However, further steps of the method 100 can be provided in step 128.

Further, the method in this example comprises step 130, which comprises at least step 102 and is carried out with the second object. Step 102 is carried out by means of a radiographic measurement of the second object. However, further steps of the method 100 can be provided in step 130.

In a further step 132, imaging parameter sets of the device are determined. To determine the imaging parameter sets, the imaging parameters of the measurement data of the first object, which are combined as imaging parameter sets, and the imaging parameters of the measurement data of the second object, which are combined as imaging parameter sets, are compared with each other. Imaging parameter sets that are identical for the measurement data of both objects are selected as the imaging parameter sets to be determined. That is, if measurement data of the first object and measurement data of the second object were determined with identical imaging parameters, the imaging parameter sets underlying this measurement data are determined by step 132. For example, if the same position of a detector and a radiation source, that is, the same radiographic geometry, were used for acquiring measurement data for both objects, with the same voltages, currents, etc., they will be identical imaging parameters.

In a further step 134, the measurement data of the first and second object associated with the determined imaging parameter sets are used to create first projection representations of the first object and second projection representations of the second object. In a further step, 136 quality parameters are determined for the first projection representations and the second projection representations and analyzed for differences. First quality parameters are determined for the first projection representations and second quality parameters are determined for the second projection representation.

In an alternative or additional example of the method 100 according to FIG. 3*b*, imaging parameter sets of the device can be defined in a step 138 for determining the measurement data.

These imaging parameter sets are used in step 140 to acquire measurement data from the first object in order to obtain first projection representations. Step 140 comprises at least step 102, which is carried out with the first object. The underlying measurement is a radiographic measurement. However, further steps of the method 100 mentioned above can be used.

In step 142, these imaging parameter sets are used to acquire measurement data from the second object to obtain a second projection representation. Step 142 comprises at least step 102, which is carried out with the second object. The underlying measurement is a radiographic measurement. However, further steps of the method 100 mentioned above can be used.

Further, at least one first quality parameter of the first projection representations and at least one second quality parameter of the second projection representation are also determined. In step 144, the first quality parameters and second quality parameters are analyzed for differences.

The comparison between the first quality parameter and the second quality parameter allows the functional status of the device for investigating objects to be analyzed. Since quality parameters based on the same imaging parameter sets are compared to each other, the quality parameters of the measurement data of the two objects should be at least similar. If there are differences, this indicates that the functional status of the device for investigating objects has changed between the measurement of the first object and the second object. The measurements of the first object and the second object can take place a long time apart. This means that a change in the functional status can be investigated over a long period of time.

FIG. 4 shows another alternative or additional exemplary embodiment of the computer-implemented method 100, in which a first and a second object are measured in order to analyze the functional status of the device for investigating objects.

In step 146 this example comprises at least step 102, which is carried out with the first object. However, further steps of the method 100 may also be provided. The measurement used is a radiographic measurement.

In step 148 this example comprises at least step 102, which is carried out with the second object. However, further steps of the method 100 may also be provided. The measurement used is a radiographic measurement. In step 102 a different radiographic geometry is used for the second object than for the first object.

In step 150, projection representations are determined from the measurement data of the first object. Then in step 152, projection representations are also determined from the measurement data of the second object.

The projection representations of the first object and the projection representation of the second object are analyzed and a blurring of the projection representations is determined in each case. Step 154 compares the blurring of the projection representations of the first object and the blurring of the projection representation of the second object.

In step 156, the blurring of the first projection representation and the blurring of the second projection representation are analyzed to determine the status characteristic value. Since the blurring of projection images remains comparable over many measurements, regardless of the nature of the geometry of the scanned object, a change in the blurring between the two projection representations can be attributed to a change in the remaining influencing variables that vary between the measurements. In this way, a fault state can be detected.

The computer-implemented method 100 can be executed by means of a computer program product on a computer. The computer program product has instructions that can be executed on a computer. When these instructions are executed on a computer, they cause the computer to carry out the method.

The invention is not restricted to one of the embodiments described above, but rather may be modified in a variety of ways. All the features and advantages that emerge from the description and from the drawing, including structural details, spatial arrangements and method steps, may be essential to the invention both individually and in a wide variety of combinations.

The invention claimed is:

1. A computer-implemented method for monitoring the status of a device for investigating objects, wherein the investigation of an object involves determining measurement data by measuring the object and operating data of the device is determined during the investigation of the object, wherein the method comprises the following steps:
   determining measurement data of the object by means of the device;
   determining operating data of the device during the step of determining measurement data of the object;
   determining at least one quality parameter from the measurement data;
   analyzing the operating data and the at least one quality parameter;
   determining a status characteristic value based on the analysis of the operating data and the at least one quality parameter in order to monitor the status of the device, wherein the status characteristic value indicates a status of the device;
   carrying out at least the step of determining measurement data of the object with a first object, wherein the measurement is a radiographic measurement;
   carrying out at least the step of determining measurement data of the object with a second object, wherein the measurement is a radiographic measurement, wherein a different radiographic geometry is used than for the first object;
   determining projection representations from the measurement data of the first object;
   determining projection representations from the measurement data of the second object;
   comparing at least one blurring between the projection representations of the first object and the projection representations of the second object; and
   analyzing the at least one blurring to determine the status characteristic value.

2. The method as claimed in claim 1, wherein the step of determining a status characteristic value further comprises the following sub-step:
   comparing the operating data and the at least one quality parameter with predefined comparative values for the operating data and the at least one quality parameter for determining a status characteristic value.

3. The method as claimed in claim 1, wherein the step of determining a status characteristic value further comprises the following sub-step:
   comparing the operating data and the at least one quality parameter to predetermined sample data for the operating data, derived from training data, and for the at least one quality parameter for determining a status characteristic value.

4. The method as claimed in claim 3, wherein the training data is generated from measurement data which is determined by means of the device by means of at least one measurement within a predefined time interval before and/or after determining measurement data of a reference object, wherein the reference object has a known geometry and/or a known property.

5. The method as claimed in claim 1, wherein the step of determining a status characteristic value further comprises the following sub-step:
   determining whether the status characteristic value indicates a fault state of the device.

6. The method as claimed in claim 5, wherein the method further comprises the following steps if the status characteristic value indicates that a fault state of the device might be present:
   determining measurement data of a reference object by means of the device; and
   analyzing the measurement data of the reference object to determine information on whether the fault state of the device is present.

7. The method as claimed in claim 1, wherein the method further comprises the following step:
   determining a fault cause parameter at least from the status characteristic value, wherein the fault cause parameter indicates a possible cause of the fault for a fault state.

8. The method as claimed in claim 7, wherein, if in the step of determining a fault cause parameter, a fault cause parameter is determined which indicates that a geometric calibration of the device has an accuracy value that is outside a predefined accuracy value interval, the method further comprises the following step:
   calibrating the device.

9. The method as claimed in claim 8, wherein the device comprises an automatic object exchange unit, wherein the method further comprises the following step:
   substituting a reference object for the object in the device for investigating objects for determining measurement data relating to the reference object and/or substituting a calibration object for the object in the device for investigating objects to calibrate the device for investigating objects.

10. The method as claimed in claim 1, wherein the method further comprises the following steps:
    carrying out at least the step of determining measurement data of the object with a first object, wherein the measurement of the first object is a radiographic measurement;
    carrying out at least the step of determining measurement data of the object with a second object, wherein the measurement of the second object is a radiographic measurement;
    determining imaging parameter sets of the device which are identical for the determination of measurement data for the first object and for the determination of measurement data for the second object;
    determining first projection representations from the measurement data for the first object by means of the determined imaging parameter sets and determining second projection representations from the measurement data for the second object by means of the determined imaging parameter sets; and
    analyzing at least one first quality parameter assigned to one of the first projection representations, and at least one second quality parameter assigned to at least one of the second projection representations, for differences; and/or that the method further comprises the following steps if an imaging parameter set of a first object and an imaging parameter set of a second object are at least partly non-identical:
  defining imaging parameter sets of the device for determining measurement data;
  carrying out at least the step of determining measurement data of the object with a first object with the defined imaging parameter sets for determining first projection representations, wherein the measurement is a radiographic measurement;
  carrying out at least the step of determining measurement data of the object with a second object, with the defined imaging parameter sets for determining second projection representations, wherein the measurement is a radiographic measurement; and
  analyzing at least one first quality parameter assigned to one of the first projection representations, and at least one second quality parameter assigned to at least one of the second projection representations, for differences;
wherein a geometry of the second object deviates from a geometry of the first object within a predefined tolerance interval.

11. The method as claimed in claim 1, wherein the method further comprises the following step:
  determining an estimate of an uncertainty of a measurement variable of the object determined from the measurement data by means of the operating data and the at least one quality parameter.

12. The method as claimed in claim 1, wherein during the step of determining measurement data of the object by means of the device, the following steps are carried out:
  determining preliminary measurement data and/or at least one preliminary quality parameter from the measurement data; and
  adapting the step of determining measurement data of the object by means of the device, taking the preliminary measurement data and/or the at least one preliminary quality parameter from the measurement data into account.

13. The method as claimed in claim 12, wherein the method further comprises the following step:
  determining whether a measurement variable of the object determined from the measurement data, preferably taking an uncertainty of the measurement variable into account, lies within a predefined tolerance range.

14. A non-transitory computer program product that contains instructions that can be executed on a computer, which when executed on a computer cause the computer to carry out the method as claimed in claim 1.

* * * * *